United States Patent [19]

Grollier et al.

[11] Patent Number: 4,981,486

[45] Date of Patent: Jan. 1, 1991

[54] NITRO BENZENE DYE, THE PROCESS FOR PREPARATION THEREOF AND ITS USE IN DYEING KERATINOUS FIBRES

[75] Inventors: Jean F. Grollier, Paris; Jean Cotteret, Limay; Alex Junino, Livry Gargan; Alain Genet, Neuilly-Plaisance, all of France

[73] Assignee: L'Oreal, Paris, France

[21] Appl. No.: 773,367

[22] Filed: Sep. 6, 1985

[30] Foreign Application Priority Data

Sep. 17, 1984 [LU] Luxembourg ............................ 85541

[51] Int. Cl.$^5$ ....................... A61K 7/13; C07C 211/51
[52] U.S. Cl. ........................................... 8/415; 8/414; 8/408; 564/441
[58] Field of Search ............................ 564/441; 8/415

[56] References Cited

U.S. PATENT DOCUMENTS 3,733,175   5/1973   Alperin et al. .......................... 8/415

FOREIGN PATENT DOCUMENTS

| | | |
|---|---|---|
| 1051605 | 9/1953 | France . |
| 1101904 | 4/1955 | France . |
| 1581135 | 8/1969 | France . |
| 479302 | 10/1968 | Switzerland . |
| 741334 | 11/1955 | United Kingdom . |
| 2082207 | 3/1982 | United Kingdom . |
| 2112818 | 7/1983 | United Kingdom . |

*Primary Examiner*—Glennon H. Hollrah
*Attorney, Agent, or Firm*—Cushman, Darby & Cushman

[57] ABSTRACT

The present invention relates to the new nitro bezene dye of formula:

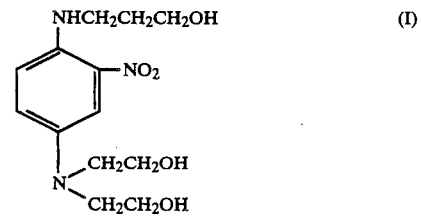

and the cosmetically acceptable salts of this compound, as well as the process for preparation thereof by condensation of 3-amino-1-propanol with 2-fluoro-5-bis(β-hydroxyethyl)amino-1-nitrobenzene.

This blue dye shows excellent solubility in water, a water/alcohol mixture and the usual dyeing media. Furthermore, when used in combination with one or more yellow nitro benzene dyes and optionally other direct dyes, it gives, especially on hair sensitized by treatment such as bleaching or permanent waving, natural shades having good lightfastness and washing resistance.

22 Claims, No Drawings

NITRO BENZENE DYE, THE PROCESS FOR PREPARATION THEREOF AND ITS USE IN DYEING KERATINOUS FIBRES

The present invention relates to a new nitrobenzene dye intended for dyeing keratinous fibers, and especially human hair.

In the field of hair dyeing, the use of direct dyes is very widespread, since they have certain advantages as compared with the precursors of oxidation dyes and, in particular, they show a decrease in the potential risks of allergy and the absence of sensitization of the hair due to the oxidative process.

Among the direct dyes which are most used, nitro benzene derivatives are found, which, on the one hand show a high affinity for the hair, and which on the other hand, as a result of the variety of possible substituents, enable a wide range of shades to be covered, ranging from yellow to blue by way of red.

Among the blue or blue-purple nitro dyes used, special mention should be made of 2-(β-hydroxyethyl)amino-5-bis(β-hydroxyethyl)amino-1-nitrobenzene (compound A), used in U.S. Pat. No. 3,733,175 or French Patent No. 2,488,133, in combination with a yellow nitro dye.

However, the formulation of this compound A causes problems on account of its limited solubility in the usual dyeing media.

The Applicants hence sought another blue nitro benzene dye having excellent solubility in water in a water/alcohol mixture and more generally in the usual dyeing media and leading, on the hair, to dyeings stable to light, washing and weathering.

As a result of this research, the Applicants discovered the new nitro benzene derivative of the formula:

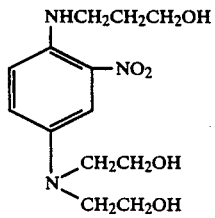

which can be used in free or salified form.

Furthermore, the Applicants observed that, surprisingly, the blue dye of formula (I) leads, when used in combination with one or more yellow or green-yellow dyes, in particular on hair sensitized by a treatment such as bleaching or permanent waving, to natural shades more lightfast and washing-resistant than the dye A.

The present invention thus has as its subject 2-(γ-hydroxypropyl)amino-5-bis(β-hydroxyethyl)amino-1-nitrobenzene of formula (I), as well as its cosmetically acceptable salts.

The present invention also has as its subject the process for preparing this compound.

The compound of formula (I) is prepared by condensing 3-amino-1-propanol with 2-fluoro-5-bis(β-hydroxyethyl)amino-1-nitrobenzene, by heating on a boiling waterbath. After the reaction mixture is cooled and neutralized, an oil is obtained by extraction, from which the expected product is precipitated.

Another subject of the present invention consists of a dyeing composition for direct dyeing of keratinous fibers, and especially human hair, containing, in an aqueous, alcoholic or hydroalcoholic vehicle, the compound of formula (I) or one of its cosmetically acceptable salts.

In a preferred form, the dyeing composition according to the invention contains the compound of formula (I) or one of its cosmetically acceptable salts in combination with one or more yellow or green-yellow nitro benzene dyes, giving, on hair which is 90% white and sensitized by permanent waving, a shade or hue between 2.5 Y and 2.5 GY on the Munsell circle (see publication of Official Digest, April 1964, page 375, FIG. 2).

According to a more especially preferred embodiment of the present invention, the compound of formula (I) is combined with yellow or green-yellow dyes belonging to the classes defined by the following formulae:

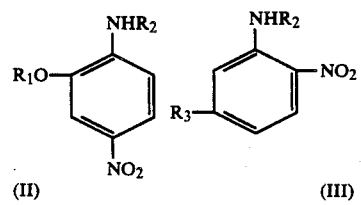

in which $R^1$ and $R^2$ denote a $C_1$ to $C_4$-alkyl or $C_2$ to $C_4$-mono- or polyhydroxyalkyl radical, and $R^3$ denotes a hydrogen atom, a $C_1$ to $C_4$ alkoxy radical or a $C_1$ to $C_4$-mono- or polyhydroxyalkoxy radical.

The preferred compounds of formula (II) are as follows:
3-methoxy-4-(β-hydroxyethyl)amino-1-nitrobenzene.
3-(β-hydroxyethyloxy)-4-(β-hydroxyethyl)amino-1-nitrobenzene.

Preferred dyes of formula (III) are as follows:
2-methylamino-4-(β-hydroxyethyloxy)-1-nitrobenzene
2-methylamino-4-(β,γ-dihydroxypropyloxy)-1-nitrobenzene
2-(β-hydroxyethyl)amino-1-nitrobenzene.

According to the invention, the concentration of compound of formula (I) is between 0.1 and 5% by weight, expressed as free base.

The total concentration of compounds of formula (II) and/or (III) is between 0.05 and 3% by weight.

It is of course possible to add to the blue dye/yellow dyes combinations according to the invention other nitro benzene dyes which do not belong to the range of yellow or green-yellow dyes giving, on hair which is 90% white and sensitized by permanent waving, a shade or hue between 2.5 Y and 2.5 GY on the Munsell circle.

It is also possible to add other direct dyes, other than nitro benzene dyes, such as azo or anthraquinone dyes, triarylmethane dyes or basic dyes such as dyes known by the name "Basic Brown 16", "Basic Yellow 57", "Basic Red 76" and "Basic Blue 99" in the COLOUR INDEX, 3rd edition.

The proportion of these additional dyes, nitro benzene or other dyes, can vary between 0.05 and 10% by weight of the composition.

The dyeing compositions according to the invention can contain, as a suitable vehicle, water and/or organic solvents acceptable from the cosmetic standpoint, and more especially alcohols such as ethyl alcohol, isopropyl alcohol, benzyl alcohol and phenylethyl alcohol or glycols or glycol ethers such as, for example, ethylene glycol and its monomethyl, monoethyl and monobutyl ethers, propylene glycol, butylene glycol and dipropylene glycol, as well as alkyl ethers of diethylene glycol, such as, for example, diethylene glycol monoethyl ether or monobutyl ether, in concentrations between 0.5 and 20%, and preferably between 2 and 10%, by weight relative to the total weight of the composition.

It is also possible to add to the composition according to the invention fatty amides, such as mono- and diethanolamides of acids derived from copra, of lauric acid or oleic acid, at concentrations between 0.5 and 10% by weight.

It is also possible to add to the composition according to the invention anionic, cationic, nonionic or amphoteric surfactants, or mixtures thereof. The surfactants are preferably present in the composition according to the invention in a proportion between 0.1 and 50% by weight, and advantageously between 1 and 20% by weight, relative to the total weight of the composition.

Among surfactants, special mention may be made of anionic surfactants used alone or mixed, such as, in particular, the alkali metal salts, magnesium salts, ammonium salts, amine salts or alkanolamine salts of the following compounds:

alkyl sulphates, alkyl ether sulphates, ethoxylated or non-ethoxylated alkylamide sulphates, alkylsulphonates, alkylamide-sulphonates, alpha-olefinsulphonates;

alkyl sulphoacetates;

fatty acids such as lauric, myristic, oleic, ricinoleic, palmitic and stearic acids, coconut oil acid or hydrogenated coconut oil acid, and carboxylic acids of polyglycol ethers, the alkyl radicals of these compounds having a straight chain of 12 to 18 carbon atoms.

By way of cationic surfactants, more special mention may be made of the salts of fatty amines, quaternary ammonium salts such as alkyldimethylbenzylammonium, alkyltrimethylammonium, alkyldimethylhydroxyethylammonium and dimethyldialkylammonium chlorides and bromides, alkylpyridinium salts and imidazoline derivatives. The alkyl groups of the abovementioned quaternary ammonium derivatives are long chain groups preferably having between 12 and 18 carbon atoms.

Amine oxides may also be mentioned among these compounds having cationic nature.

Among amphoteric surfactants which can be used, special mention may be made of alkylamino-(mono- and di-)propionates, betaines such as alkylbetaines, N-alkylsulphobetaines, and N-alkylaminobetaines, the alkyl radical having between 1 and 22 carbon atoms, and cycloimidinium compounds such as alkylimidazolines.

Among nonionic surfactants which can optionally be used in the compositions according to the invention, mention may be made of the products of condensation of a monoalcohol, α-diol, alkylphenol or amide with glycidol or a precursor of glycidol, such as the compounds corresponding to the following formulae:

R—CHOH—CH$_2$—O—(CH$_2$—CHOH—CH$_2$—O)$_n$H in which R denotes an aliphatic, cycloaliphatic or arylaliphatic radical having 7 to 21 carbon atoms, and the mixtures thereof, the aliphatic chains being able to contain ether, thioether and hydroxymethylene groups, and n being an integer such that $1 \leq n \leq 10$;

RO—[C$_2$H$_3$O—(CH$_2$OH)$_m$]—H in which R denotes an alkyl, alkenyl or alkylaryl radical having 8 to 22 carbon atoms and $1 \leq m \leq 10$;

polyethoxylated or polyglycerolated alcohols, alkylphenols or fatty acids having a C$_8$ to C$_{18}$ linear fatty chain;

condensates of ethylene oxide and propylene oxide with fatty alcohols; polyethoxylated fatty amides containing at least 5 moles of ethylene oxide;

polyethoxylated fatty amines.

The thickeners which can be added to the composition according to the invention can advantageously be chosen from the group consisting of sodium alginate, gum arabic, guar gum, cellulose derivatives such as methylcellulose, hydroxyethylcellulose, hydroxypropylmethylcellulose and the sodium salt of carboxymethylcellulose, and acrylic acid polymers.

Inorganic thickening agents such as bentonite can also be used. These thickeners are used alone or mixed, and are preferably present in a proportion between 0.5 and 5% by weight relative to the total weight of the composition, and advantageously between 0.5 and 3% by weight.

The dyeing compositions according to the invention can be formulated at an acid, neutral or alkaline pH, the pH being able to vary from 4 to 10.5, and preferably from 6 to 10. Among the alkalinizing agents which can be used, alkanolamines and alkali metal or ammonium hydroxides and carbonates may be mentioned. Among the acidifying agents which can be used, lactic acid, acetic acid, tartaric acid, phosphoric acid, hydrochloric acid and citric acid may be mentioned.

The dyeing compositions can contain, in addition, various common adjuvants such as antioxidants, perfumes, sequestering agents, film-forming products, treatment agents, dispersants, hair conditioning agents, preservatives and opacifiers, as well as any other adjuvant customarily used in cosmetics.

The dyeing composition according to the invention can be presented in the various usual forms for hair dyeing, such as thickened or gellified liquids, creams, aerosol foams or in all other forms suitable for carrying out dyeing of keratinous fibers.

The present invention also has as its subject a new process for dyeing keratinous fibers, and especially human hair, characterised in that the dyeing composition defined above is allowed to act on the dry or damp keratinous fibers. The compositions according to the invention can be used as non-rinse lotions, that is to say the compositions according to the invention are applied on the keratinous fibers which are then dried without intermediate rinsing. In other modes of application, the dyeing compositions according to the invention are applied on the keratinous fibers for an exposure time varying between 3 and 60 minutes, preferably between 5 and 45 minutes, and the fibers are then rinsed, optionally washed, rinsed again and dried.

The dyeing compositions according to the invention can be applied on natural or dyed hair, permanently-waved or otherwise, or on hair which has been strongly or slightly bleached and optionally permanently waved.

To enable the subject of the invention to be more clearly understood, several modes of use will now be described, by way of purely illustrative and non-limitative example.

Preparation of
2-(σ-hydroxypropyl)amino-5-bis(β-hydroxyethyl)amino-1-nitrobenzene monohydrochloride

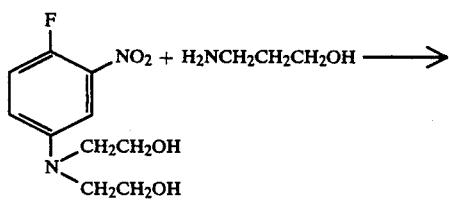

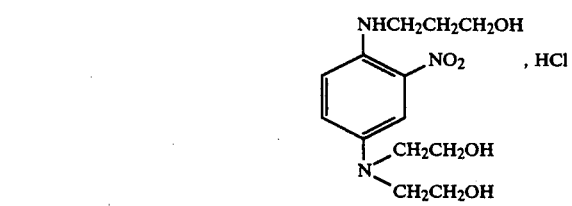

In 60 ml of 3-amino-1-propanol, 0.07 mole (17.1 g) of 2-fluoro-5-bis(β-hydroxyethyl)amino-1-nitrobenzene are dissolved with stirring. After 3/4 hour of heating on a boiling waterbath, the reaction medium is poured onto 300 g of ice. The majority of the 3-amino-1-propanol is neutralized by adding 35 ml of concentrated hydrochloric acid.

After extraction with ethyl acetate, drying and evaporation of the ethyl acetate under vacuum, a violet oil is obtained which is dissolved in 100 ml of absolute ethanol. The addition of 25 ml of a solution of hydrochloric acid in absolute ethanol enables the hydrochloride of the expected product to be precipitated.

The hydrochloride is drained and washed with isopropanol. After recrystallization in 110 ml of absolute ethanol, 0.52 mole (17.4 g) of the expected product is obtained.

Molecular mass calculated for $C_{13}H_{22}N_3O_5Cl$: 335.8
Molecular mass found by potentiometric assay in water by sodium hydroxide 333.5

Analysis of the product obtained gives the following results:

| Analysis | Calculated for $C_{13}H_{22}N_3O_5Cl$ | Found |
| --- | --- | --- |
| % C | 46.5 | 46.48 |
| % H | 6.6 | 6.59 |
| % N | 12.51 | 12.38 |
| % O | 23.82 | 24.00 |
| % Cl | 10.56 | 10.40 |

EXAMPLE 1

The following dyeing composition is prepared:

| | |
| --- | --- |
| 2-(γ-Hydroxypropyl)amino-5-bis(β-hydroxyethyl)amino-1-nitrobenzene monohydrochloride | 3.0 g |
| 2-Methylamino-4-(β,γ-dihydroxypropyloxy)-1-nitrobenzene | 0.5 g |
| 2-Methylamino-4-(β-hydroxyethyloxy)-1-nitrobenzene | 0.12 g |
| 3-Methoxy-4-(β-hydroxyethyl)amino-1-nitrobenzene | 0.05 g |
| Celliton extra blue (BASF) | 0.1 g |
| Acetoquinone dark blue 5R (PCUK) | 0.1 g |
| Diazoacetoquinone black BSNZ (ICI-FRANCOLOR) | 0.2 g |
| Lauric acid | 1.0 g |
| Oleic diethanolamide | 3.0 g |
| 2-Butoxyethanol | 5.0 g |
| Ethomeen HT60 (AKZO) | 3.5 g |
| Hydroxyethylcellulose "Cellosize WPO3H" (UNION CARBIDE) | 2.0 g |
| Monoethanolamine q.s. pH 9.5 | |
| Demineralized water q.s. | 100 g |

This composition is applied on natural dark chestnut-colored hair having a small percentage of white hair. After 30 minutes' exposure and rinsing, the dried hair is brown in color and the white hair is well concealed.

EXAMPLE 2

The following dyeing composition is prepared:

| | |
| --- | --- |
| 2-(γ-Hydroxypropyl)amino-5-bis(β-hydroxyethyl)amino-1-nitrobenzene monohydrochloride | 0.6 g |
| 2-Methylamino-4-(β,γ-dihydroxypropyloxy)-1-nitrobenzene | 0.06 g |
| 2-Methylamino-4-(β-hydroxyethyloxy)-1-nitrobenzene | 0.1 g |
| 2-(β-Hydroxyethyl)amino-5-hydroxy-1-nitrobenzene | 0.05 g |
| Celliton extra blue (BASF) | 0.05 g |
| Diazoacetoquinone black BSNZ (ICI-FRANCOLOR) | 0.04 g |
| Lauric acid | 1.0 g |
| Oleic diethanolamide | 3.0 g |
| 2-Butoxyethanol | 5.0 g |
| Ethomeen HT60 (AKZO) | 3.5 g |
| Cellosize WPO3H (UNION CARBIDE) | 2.0 g |
| 2-Amino-2-metyl-1-propanol q.s. pH 9.5 | |
| Demineralized water q.s. | 100 g |

This liquid composition is applied for 30 minutes in blond hair having its color weakened by sea water and sunshine. After being rinsed and dried, the hair is dyed a homogeneous, natural dark blond shade.

EXAMPLE 3

The following dyeing composition is prepared:

| | |
| --- | --- |
| 2-(γ-Hydroxypropyl)amino-5-bis(β-hydroxyethyl)amino-1-nitrobenzene | 1.0 g |
| 3-(β-Hydroxyethoxy)-4-(β-hydroxyethyl)-amino-1-nitrobenzene | 0.05 g |
| 2-(β-Hydroxyethyl)amino-1-nitrobenzene | 0.25 g |
| 2-(β-Hydroxyethyl)amino-5-hydroxy-1-nitrobenzene | 0.1 g |
| 2-(β-Hydroxyethyl)amino-5-(β,γ-dihydroxypropyloxy)-1-nitrobenzene | 0.15 g |
| Nonylphenol treated with 9 moles of ethylene oxide | 8.0 g |
| Lauric diethanolamide | 2.0 g |
| 2-Ethoxyethanol | 10.0 g |
| 2-Amino-2-methyl-1-propanol q.s. pH 9 | |
| Demineralized water q.s. | 100 g |

This composition is applied on light chestnut-colored hair. After a fixed exposure time of 30 minutes, the hair is rinsed. The dried hair is dyed a dark auburn, golden, light chestnut shade.

EXAMPLE 4

The following dyeing composition is prepared:

| | |
| --- | --- |
| 2-(γ-Hydroxypropyl)amino-5-bis(β-hydroxyethyl)amino-1-nitrobenzene | 0.7 g |
| 3-(β-Hydroxyethyloxy)-4-(β-hydroxyethyl)amino-1-nitrobenzene | 0.1 g |

| | |
|---|---|
| 2-Methylamino-4-(β,γ-dihydroxypropyloxy)-1-nitrobenzene | 0.25 g |
| 2-Amino-4-methyl-5-(β-hydroxyethyl)-amino-1-nitrobenzene | 0.05 g |
| 2-Amino-5-(β-hydroxyethyl)-amino-1-nitrobenzene | 0.1 g |
| Nonylphenol treated with 9 moles of ethylene oxide | 8.0 g |
| Lauric diethanolamide | 2.0 g |
| 2-Ethoxyethanol | 10.0 g |
| 2-Amino-2-methyl-1-propanol q.s. pH 9 | |
| Demineralized water q.s. | 100 g |

This liquid composition is applied for 30 minutes on dark blond hair. The hair is rinsed and then dried. The latter is colored an iridescent dark blond shade.

EXAMPLE 5

The following dyeing composition is prepared:

| | |
|---|---|
| 2-(γ-Hydroxypropyl)amino-5-bis(β-hydroxyethyl)amino-1-nitrobenzene monohydrochloride | 0.65 g |
| 3-(β-Hydroxyethyloxy)-4-(β-hydroxyethyl)-amino-1-nitrobenzene | 0.15 g |
| 2-(β-Hydroxyethyl)amino-1-nitrobenzene | 0.08 g |
| Nonylphenol treated with 9 moles of ethylene oxide | 8.0 g |
| Lauric diethanolamide | 2.0 g |
| 2-Ethoxyethanol | 10.0 g |
| Monoethanolamine | 0.3 g |
| Demineralized water q.s. | 100 g |

This composition is applied on permanently waved grey hair. After 20 minutes' exposure, the hair is rinsed and then dried. The hair is dyed a light chestnut shade.

EXAMPLE 6

The following dyeing composition is prepared:

| | |
|---|---|
| 2-(γ-Hydroxypropyl)amino-5-bis(β-hydroxyethyl)amino-1-nitrobenzene monohydrochloride | 2.0 g |
| Nonylphenol treated with 9 moles of ethylene oxide | 8.0 g |
| Lauric diethanolamide | 2.0 g |
| 2-Ethoxyethanol | 2.0 g |
| 2-Amino-2-methyl-1-propanol q.s. pH 9 | |
| Demineralized water q.s. | 100 g |

This composition is applied on white hair for 30 minutes. After being rinsed and dried, the hair is dyed a strong blue violet shade.

EXAMPLE 7

The following dyeing composition is prepared:

| | |
|---|---|
| 2-(γ-Hydroxypropyl)amino-5-bis(β-hydroxyethyl)amino-1-nitrobenzene | 3.0 g |
| 2-(β-Hydroxyethyl)amino-5-hydroxy-1-nitrobenzene | 0.5 g |
| Nonylphenol treated with 9 moles of ethylene oxide | 8.0 g |
| Lauric diethanolamide | 2.0 g |
| 2-Ethoxyethanol | 10.0 g |
| 2-Amino-2-methyl-1-propanol q.s. pH 9 | |
| Demineralized water q.s. | 100 g |

This liquid composition is applied on chestnut colored hair. The latter is rinsed after 20 minutes' exposure. After being dried, the hair has a purple violet glint.

We claim:

1. A nitrobenzene derivative having the formula:

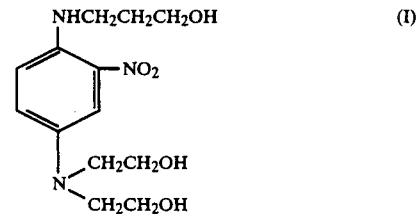

and cosmetically acceptable salts of this compound.

2. A human hair dye composition comprising in an aqueous, alcoholic or hydroalcoholic carrier a tinctorially effective amount of a nitrobenzene derivative having the formula

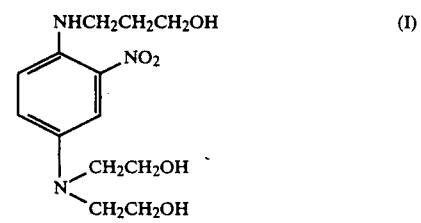

or a cosmetically acceptable salt thereof.

3. The composition of claim 1 which also includes a yellow or green-yellow nitrobenzene dye so as to produce a shade, according to Munsell, ranging between 2.5 Y and 2.5 GY on 90% white hair sensitized by permanent waving.

4. The composition of claim 3 wherein said yellow nitrobenzene dye is selected from the group consisting of (a) a dye having the formula

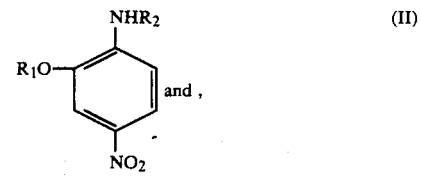

(b) a dye having the formula

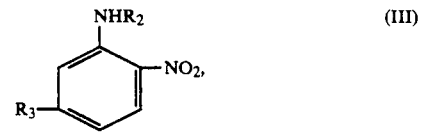

wherein $R_1$ and $R_2$ each independently represent alkyl having 1–4 carbon atoms, mono- or polyhydroxyalkoxy wherein the alkyl moiety has 2–4 carbon atoms, and $R_3$ represents hydrogen, alkoxy having 1–4 carbon atoms or mono- or polyhydroxyalkyl having 1–4 carbon atoms.

5. The composition of claim 14 wherein said nitrobenzene derivative of Formula I is present in an amount, expressed as free base, ranging from 0.1 to 5 percent by weight of said composition.

6. The composition of claim 4 wherein one or both of said dyes of Formula II and II are present in an amount ranging from 0.05 to 3 percent by weight of said composition.

7. The composition of claim 4 wherein said dye of Formula II is selected from the group consisting of 3-methoxy-4-($\beta$-hydroxyethyl) amino-1-nitrobenzene and 3-($\beta$-hydroxyethyloxy)-4-($\beta$-hydroxyethyl) amino-1-nitrobenzene.

8. The composition of claim 4 wherein said dye of Formula III is selected from the group consisting of 2-methylamino-4-($\beta$-hydroxyethyloxy)-1-nitrobenzene, 2-methylamino-4-($\beta$,$\gamma$-dihydroxypropyloxy)-1-nitrobenzene and 2-($\beta$-hydroxyethyl) amino-1-nitrobenzene.

9. The composition of claim 2 which also includes one or more of (a) a nitrobenzene dye which does not give a yellow or green-yellow shade, according to Munsell, between 2.5 Y and 2.5 GY on 90% white hair sensitized by permanent waving and (b) a direct dye selected from the group consisting of azo dye, anthraquinone dye, triarylamethane dye and basic dye, the total amount of said dyes (a) and (b) ranging from 0.05 to 10 percent by weight of said composition.

10. The composition of claim 2 containing an organic solvent selected from the group consisting of alcohol, glycol and glycol ether, said solvent being present in an amount ranging from 0.5 to 20 percent by weight of said composition.

11. The composition of claim 10 wherein said solvent is present in an amount ranging from 2 to 10 percent by weight of said composition.

12. The composition of claim 2 which also includes a fatty amide present in an amount ranging from 0.05 to 10 percent by weight of said composition.

13. The composition of claim 2 which also includes an anionic, cationic, nonionic or amphoteric surfactant, or a mixture thereof, said surfactant being present in an amount ranging from 0.1 to 50 percent by weight based on the total weight of said composition.

14. The composition of claim 13 wherein said surfactant is present in an amount ranging from 1 to 20 percent by weight based on the total weight of said composition.

15. The composition of claim 2 which also includes a thickener present in an amount ranging from 0.5 to 5 percent by weight based on the total weight of said composition.

16. The composition of claim 15 wherein said thickener is present in an amount ranging from 0.5 to 3 percent by weight based on the total weight of said composition.

17. The composition of claim 2 which also includes one or more of an antioxidant, a perfume, a sequestering agent, a film-forming agent, a treatment agent, a dispersant, a hair conditioning agent, a preservative and an opacifier.

18. The composition of claim 2 having a pH ranging from 4 to 10.5.

19. The composition of claim 2 having a pH ranging from 6 to 10.

20. A process for directing dyeing human hair comprising applying to dry or damp human hair an effective amount of the hair dye composition of claim 2 and drying said hair without an intermediate rinse thereof.

21. A process for direct dyeing human hair comprising applying an effective amount of the hair dye composition of claim 2 to said hair, permitting said hair dye composition to remain in contact with said hair for a period of time ranging from 3 to 60 minutes, rinsing the hair and drying the hair.

22. The process of claim 21 wherein said hair dye composition is permitted to remain in contact with the hair for a period of time ranging from 5 to 45 minutes.

* * * * *